(12) United States Patent
Bublick et al.

(10) Patent No.: US 9,730,829 B1
(45) Date of Patent: Aug. 15, 2017

(54) CONDOM WITH ENHANCED BASE RING

(71) Applicants: Ronald G Bublick, Virginia Beach, VA (US); Linda L Bublick, Virginia Beach, VA (US)

(72) Inventors: Ronald G Bublick, Virginia Beach, VA (US); Linda L Bublick, Virginia Beach, VA (US)

(73) Assignee: Encore Products, Inc., Virginia Beach, VA (US)

( * ) Notice: Subject to any disclaimer, the term of this patent is extended or adjusted under 35 U.S.C. 154(b) by 0 days.

(21) Appl. No.: 15/068,831

(22) Filed: Mar. 14, 2016

(51) Int. Cl.
*A61F 6/04* (2006.01)
*A61F 5/41* (2006.01)

(52) U.S. Cl.
CPC .................. *A61F 5/41* (2013.01); *A61F 6/04* (2013.01); *A61F 2005/414* (2013.01); *A61F 2006/047* (2013.01); *A61F 2006/048* (2013.01)

(58) Field of Classification Search
USPC .......................................... 128/844; 604/349
See application file for complete search history.

(56) References Cited

U.S. PATENT DOCUMENTS

| | | | | |
|---|---|---|---|---|
| 2,670,736 A * | 3/1954 | Dunkelberger | ............ | A61F 6/04 128/844 |
| 5,163,448 A * | 11/1992 | Foldesy | .................... | A61F 6/04 128/844 |
| 5,163,449 A * | 11/1992 | van der Valk | ............ | A61F 6/04 128/844 |
| 5,425,379 A * | 6/1995 | Broad, Jr. | ................. | A61F 6/04 128/842 |
| 5,855,206 A * | 1/1999 | Ireland | ...................... | A61F 6/04 128/842 |
| 5,954,054 A * | 9/1999 | Johnson | .................... | A61F 6/04 128/844 |
| 2008/0142021 A1* | 6/2008 | Hook | ........................ | A61F 6/04 128/844 |

* cited by examiner

*Primary Examiner* — Ophelia A Hawthorne
(74) *Attorney, Agent, or Firm* — Peter J. Van Bergen

(57) ABSTRACT

A condom includes an elastic ring having a radial width in the range of approximately 0.1875 inches to approximately 0.5 inches and an axial length in the range of approximately 0.1875 inches to approximately 5 inches, and a sleeve of flaccid and elastic material having an annular open end and a closed end. The sleeve is coupled to the elastic ring.

10 Claims, 4 Drawing Sheets

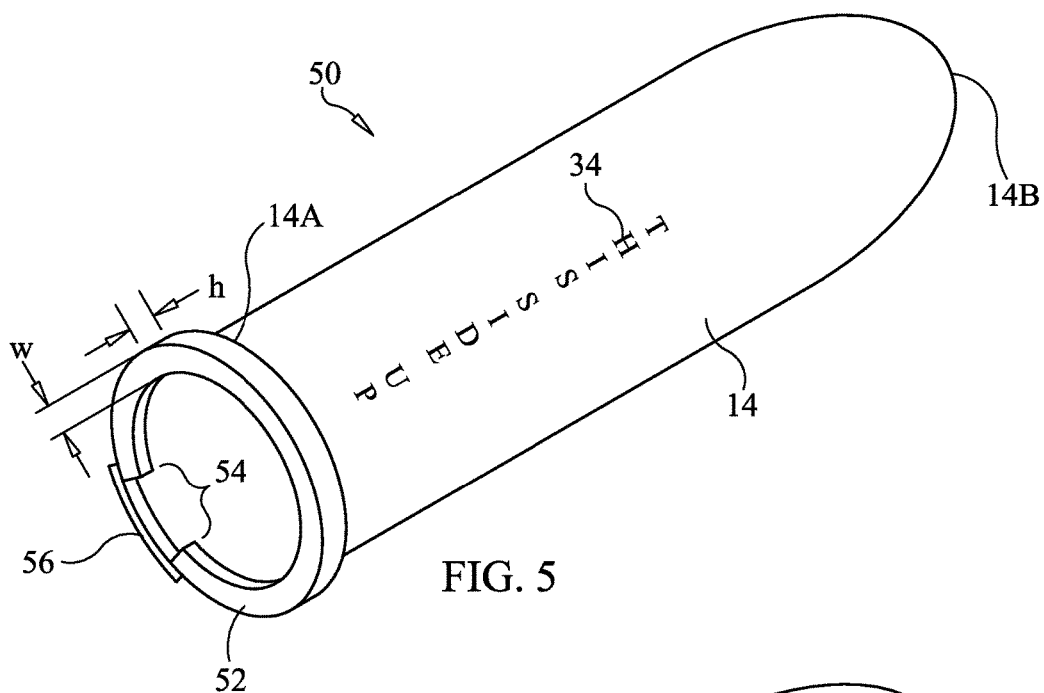
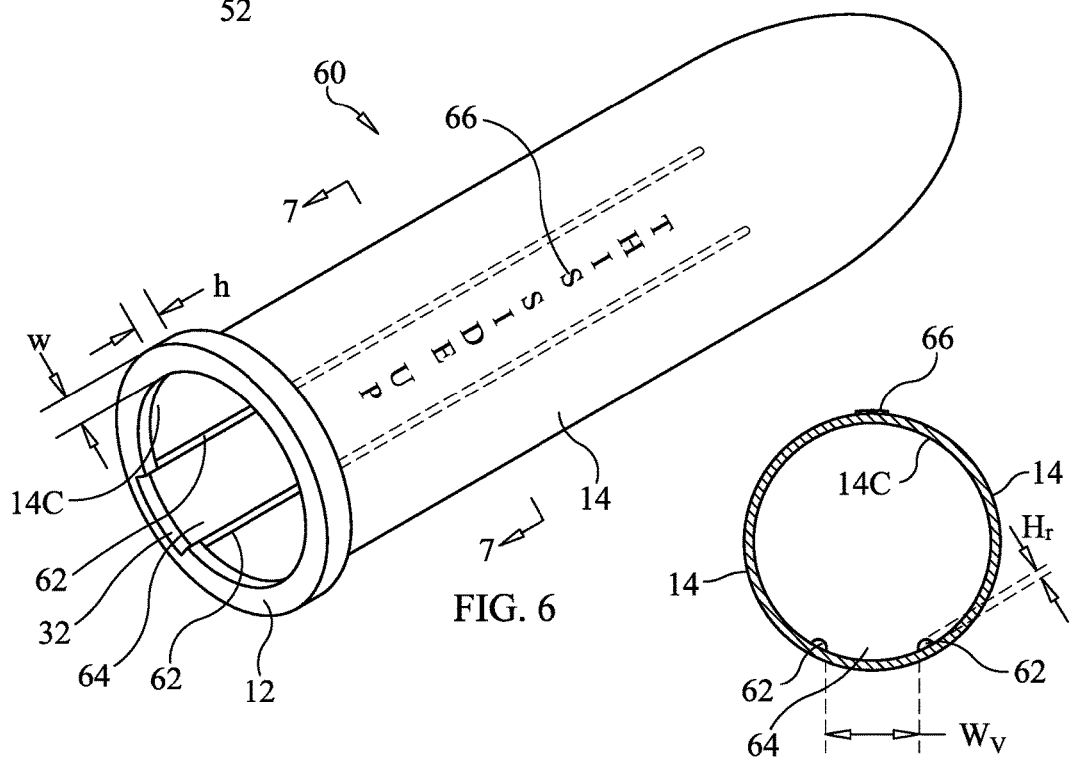

CONDOM WITH ENHANCED BASE RING

CROSS-REFERENCE TO RELATED PATENT APPLICATIONS

This patent application is co-pending with one related patent application entitled "CUFF AND CUFF/CONDOM COMBINATION FOR ERECTION ASSISTANCE", application Ser. No. 14/824,650, filed Aug. 12, 2015.

FIELD OF THE INVENTION

The invention relates generally to condoms, and more particularly to condoms having a base ring that can provide erection assistance and/or erection enhancement.

BACKGROUND OF THE INVENTION

Options for males experiencing some degree of erectile dysfunction (or "ED" as it is also known) include worn devices, surgically-implanted devices, external equipment, surgeries, and ingested medications. Surgically-implanted devices, external equipment, and ingested medications are expensive, and can present a variety of post-use health risks and/or potential side effects with ingested medications having potential adverse reactions including fatal events. Worn devices generally avoid the expense and health risks associated with implanted devices and medications. However, existing worn devices are relatively few in number, have little credibility, and have not been effective thereby leaving ED-afflicted males with no solution other than reliance on the more expensive and riskier surgeries, surgically-implanted devices and more expensive ingested medications.

SUMMARY OF THE INVENTION

Accordingly, it is an object of the present invention to provide a condom for use by a male to improve his sexual experience.

Another object of the present invention is to provide a simple and effective condom that can also provide erection assistance.

Other objects and advantages of the present invention will become more obvious hereinafter in the specification and drawings.

In accordance with the present invention, a condom includes an elastic ring having a radial width in the range of approximately 0.1875 inches to approximately 0.5 inches and an axial length in the range of approximately 0.1875 inches to approximately 5 inches, and a sleeve of flaccid and elastic material having an annular open end and a closed end. The sleeve is coupled to the elastic ring. In other embodiments of the invention, the ring can be notched and the sleeve can be marked for proper placement of the notch when the condom is worn. In yet other embodiments of the present invention, spaced-apart ridges can extend axially along the inside surface of the sleeve. In still other embodiments of the invention, one or more retention rings can be provided along the sleeve.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein:

FIG. 5 is a perspective view of a condom with an assembled enhanced base ring in accordance with another embodiment of the present invention;

FIG. 6 is a perspective view of a condom with a notched enhanced base ring and urethral tube void region in accordance with another embodiment of the present invention; and FIG. 7 is a cross-sectional view of the condom taken along line 7-7 in FIG. 6.

DETAILED DESCRIPTION OF THE INVENTION

Figure 1A:
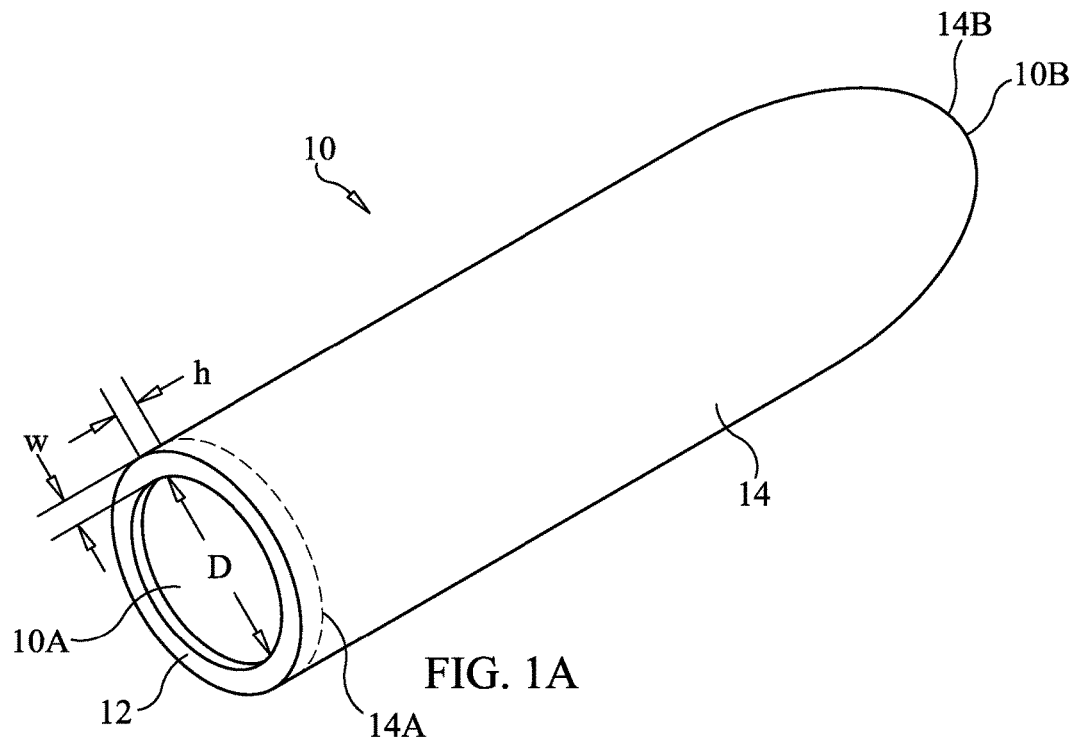
FIG. 1A is a perspective view of a condom with an enhanced base ring in accordance with an embodiment of the present invention.
Figure 1B:
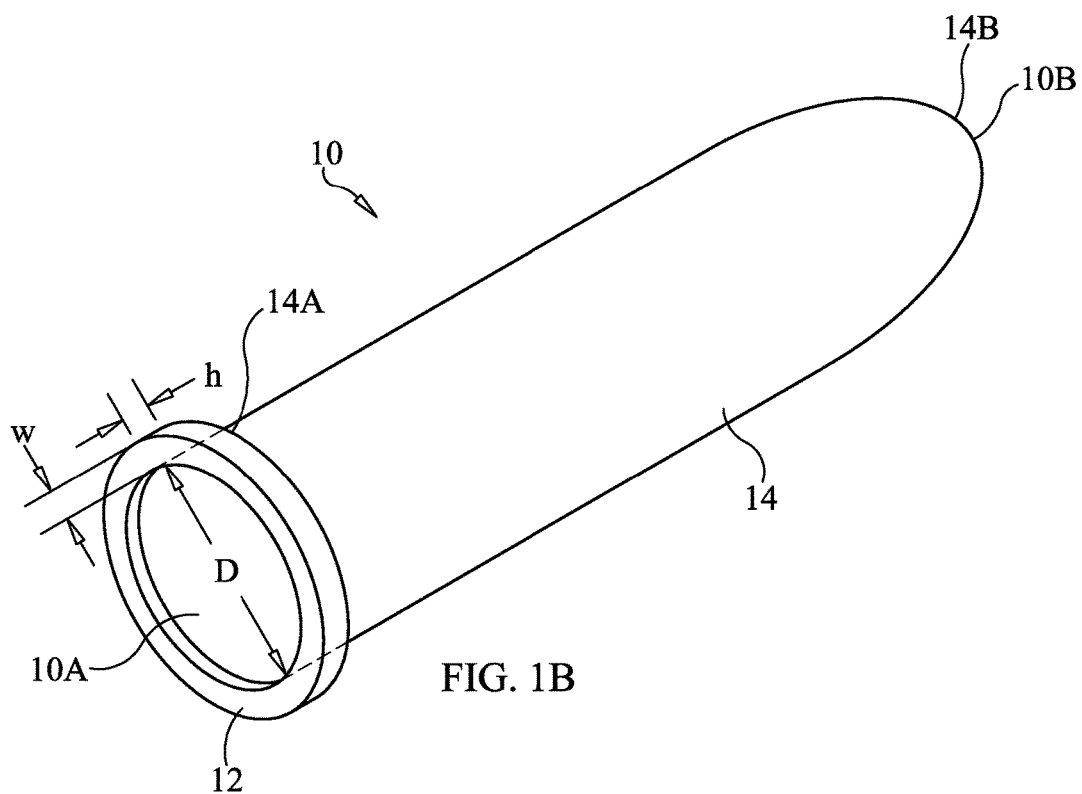
FIG. 1B is a perspective view of a condom with an enhanced base ring in accordance with another embodiment of the present invention.
Figure 1C:
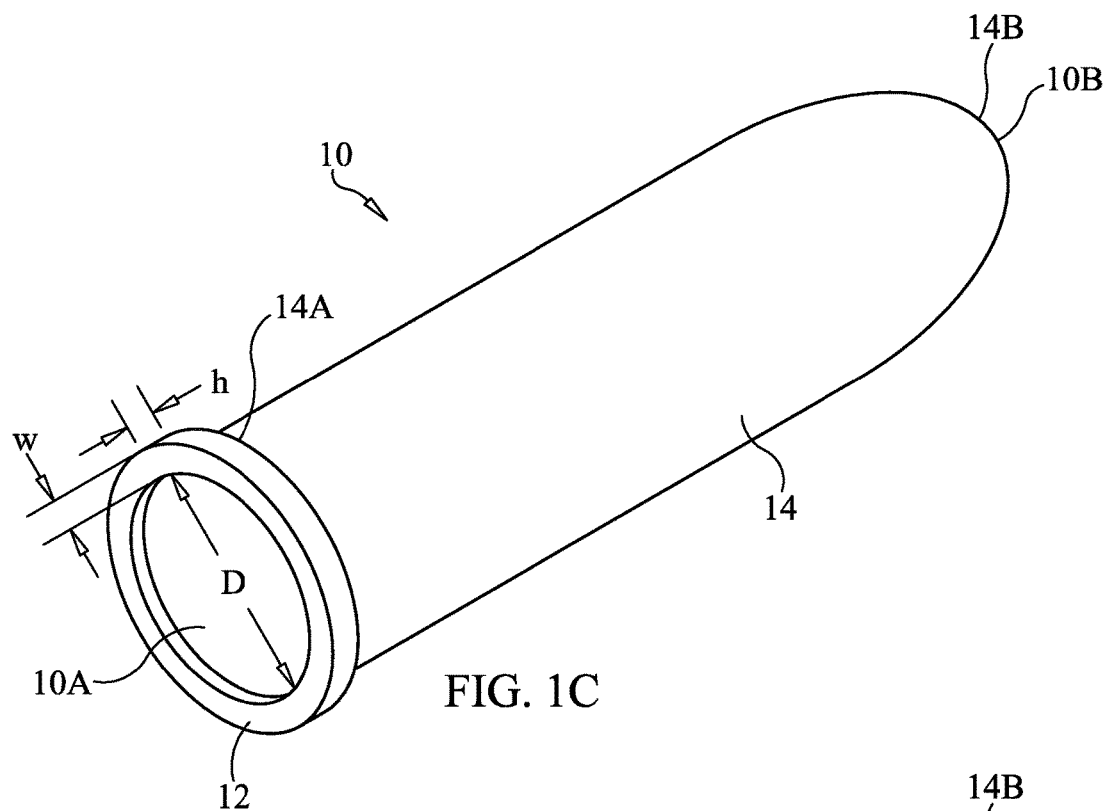
FIG. 1C is a perspective view of a condom with an enhanced base ring in accordance with still another embodiment of the present invention.

Referring now to the drawings and more particularly to FIGS. 1A-1C, a condom for use as a contraceptive device as well as a non-surgical-based and non-medicinal device that provides erection assistance for a male is shown and is referenced generally by numeral 10. Condom 10 can be used by a male experiencing some or any degree of erectile dysfunction (or "ED"), or by a male seeking a firmer and/or longer-lasting erection. Condom 10 is generally tubular in shape with one open end 10A and one closed end 10B. Open end 10A is defined by an elastic base ring 12. Coupled to ring 12 is a sleeve 14 of flaccid and elastic material defining the body and closed end 10B of condom 10. More specifically, sleeve 14 has an open annular end 14A and a closed end or tip 14B defining the closed end 10B of condom 10. Annular end 14A is coupled/sealed to ring 12 in any of a variety of ways known in the art of condom manufacturing. For example, in FIG. 1A, open annular end 14A is affixed to the outermost periphery of ring 12 such that ring 12 is essentially on the inside of sleeve 14. In FIG. 1B, open annular end 14A is affixed to the inside of periphery of ring 12 such that open annular end 14A essentially defines open end 10A of condom 10. In FIG. 1C, open annular end 14A is affixed to a portion of ring 12 between its outermost periphery and inside periphery. Tip 14B can be rounded (as shown) or shaped in other ways (e.g., to form a receptacle) without departing from the scope of the present invention. It is to be understood that the construction methods used to fabricate each embodiment of condom 10 (as well as other embodiments described or suggested herein) are not limitations of the present invention.

In general, condom 10 is placed on/over a flaccid, partially erect and/or erect male penis to thereby serve as a contraceptive device while also providing erection assistance to the wearer as will be explained later herein. As used herein, the term "erection assistance" means that condom 10 in combination with a flaccid, partially erect, or erect penis provides firmness that helps support sexual intercourse. In terms of length, condom 10 is sized to allow tip 14B to cover the head of the penis with sleeve 14 extending to the base region of the penis where ring 12 will reside. It is to be understood that ring 12 could also be positioned at other axial locations along sleeve 14 and coupled/sealed thereto, or that more than one ring 12 could be positioned at axial locations along sleeve 14 and coupled/sealed thereto, without departing from the scope of the present invention. Materials used for condom 10 can include, but are not limited to, elastic materials used in the manufacture of condoms to include latex/natural rubber, all forms of synthetic rubber, polyester, polyethylene, plastics, lambskin, and combinations thereof. As will be explained further below, ring(s) 12 is constructed to stretch outward in the radial direction such that it applies inward radial pressure to the base of a penis when used. Condom 10 could be made in one size, several general sizes, or could be specially sized such that its diameter and/or length are adapted for a specific user.

As mentioned above, ring 12 is constructed to provide a sufficient amount of radial pressure to a penis that promotes, helps attain, and/or maintains an erection. Ring 12 could also have vibrating device(s)/element(s) (not shown) coupled thereto without departing from the scope of the present invention. Ring 12 is a solid, semi-solid (e.g., made from rolled up material), or hollow-wall ring made from a material used in the manufacture of condoms. The edges of ring 12 can be angled/beveled or rounded for user comfort. In general, the height ("h") and width ("w") dimensions of ring 12 (i.e., height h being in the axial dimension of condom 10 and width w being in the radial dimension of condom 10) are significantly greater than that of the rolled material found at the open end of a conventional condom. For example, when using a condom-type of latex material for ring 12, the height h for ring 12 is in the range of approximately 0.1875 inches to approximately 5 inches (or even more for some applications) and the width w for ring 12 is in the range of approximately 0.1875 inches to approximately 0.5 inches (or even more for some applications). The inner diameter "D" of ring 12 should form a snug fit with the base of a penis. In this way, ring 12 will still be able to stretch elastically to fit onto a penis, but its above-defined height/width dimensions will also apply a greater amount of inward radial pressure to a penis as compared to a conventional condom's rolled-ring open end.

Sleeve 14 is made from a thin, elastic, flaccid material having material and dimensional attributes generally similar to those used in the manufacture of conventional condoms. For example, the wall thickness of sleeve 14 will generally be in the range of approximately 0.03 millimeters (mm) to approximately 0.09 mm.

Figure 2:
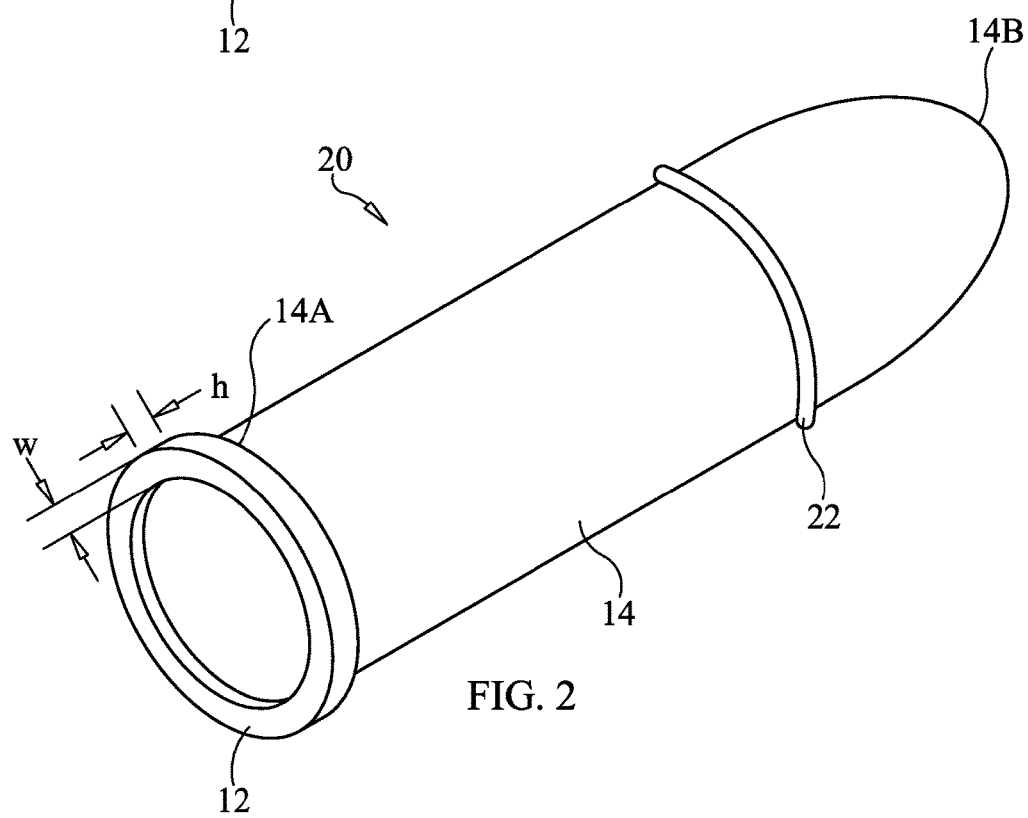
FIG. 2 is a perspective view of a condom with an enhanced base ring and a retention ring in accordance with another embodiment of the present invention.

Another embodiment of the present invention is illustrated in FIG. 2 where a condom 20 includes the elements and features of the above-described condom 10 and further includes at least one additional ring 22. For ease and clarity of illustration, condom 20 is predicated on one of the embodiments of condom 10 shown in FIGS. 1B and 1C. Ring 22 is generally made from an elastic material used in the manufacture of condoms, and is sized to snugly fit on a penis to hold/retain condom 20 in place without slippage. Ring 22 can also function to help retain blood in a penis to thereby assist in firming the penis. For example, ring 22 can be positioned such that it will reside just behind a penis' corona (i.e., the ridge around the base of the head of the penis) when condom 20 is worn. Ring 22 can be made from the same or different materials and/or colors as sleeve 14 without departing from the scope of the present invention. Ring 22 can be integrally fabricated with sleeve 14 or fabricated separately from sleeve 14 and then placed thereon, or attached/adhered thereto without departing from the scope of the present invention. Ring 22 could be formed by a rolled amount of the material used for sleeve 14 similar to the rolled ring end of a conventional condom. The position of ring 22 can be different than that shown. Further, additional rings similar to ring 22 could be included without departing from the scope of the present invention. Still further and as mentioned above, the structure of ring 22 can be the same as previously-described ring 12.

Figure 3:
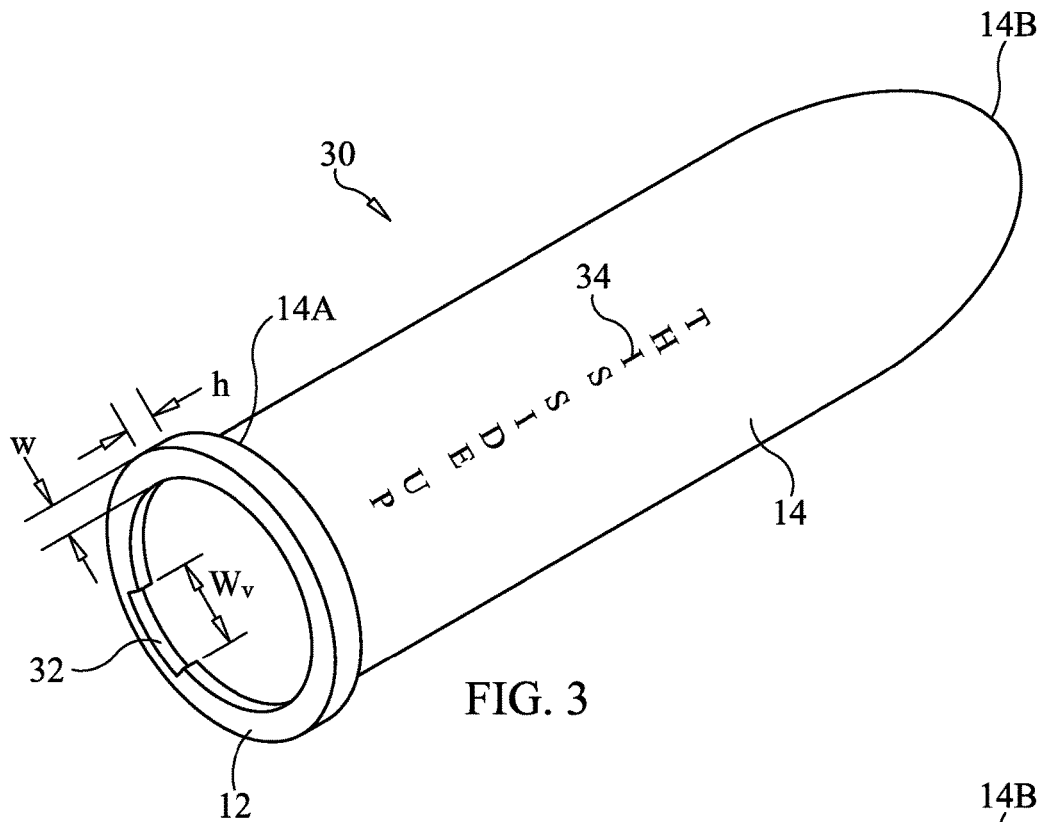
FIG. 3 is a perspective view of a condom with a notched enhanced base ring in accordance with another embodiment of the present invention.

Still another embodiment of the present invention is illustrated in FIG. 3 where a condom 30 includes the elements and features of the above-described condom 10 and further includes a notch 32 in ring 12. Once again, for ease and clarity of illustration, condom 30 is predicated on one of the embodiments of condom 10 shown in FIGS. 1B and 1C. More specifically, ring 12 in condom 30 is a monolithic ring with notch 32 being cut partially into ring 12 such that notch 32 defines a radial arc-shaped gap that faces radially inward. When condom 30 is worn, the gap defined by notch 32 should be aligned with the wearer's urethral tube that runs along the length of the underside of the penis. When aligned with the wearer's urethral tube, notch 32 defines a region of condom 30 along which little to no inward radial pressure will be applied to the wearer's penis. The width $W_v$ of notch 32 can be in the range of approximately 0.125 inches to approximately 0.75 inches with the larger widths providing a spacing that accommodates slight misalignment and anatomical differences between users. If an additional ring 12 with notch 32 is used, all ring notches should be in axial alignment along the length of sleeve 14.

To provide alignment guidance, sleeve 14 can include visual and/or tactile indicia to assist with alignment of condom 30. For example, the illustrated embodiment's indicia includes verbiage 34 (e.g., "THIS SIDE UP" as shown) indicating the top of condom 30 (as viewed when worn). Verbiage 34 is located in diametric opposition to notch 32 to facilitate alignment of notch 32 with the wearer's urethral tube. Verbiage 34 can be printed letters, and/or can be formed by raised letters, shapes, etc., to provide a tactile indicator for proper alignment. Verbiage 34 (and/or tactile indicia) can be provided on the outside and/or inside surface of sleeve 14, and can be of a color that is the same or different from the color used for sleeve 14, without departing from the scope of the present invention. The inward radial pressure provided by the enhanced base ring 12 of the present invention (and, if present, the one or more additional rings 22) provides erection assistance and/or additional penile firming forces to a flaccid, partially erect, or erect penis, while notch 32 provides for reduced impediment of seminal or other body fluids flow through the urethral tube.

Figure 4:
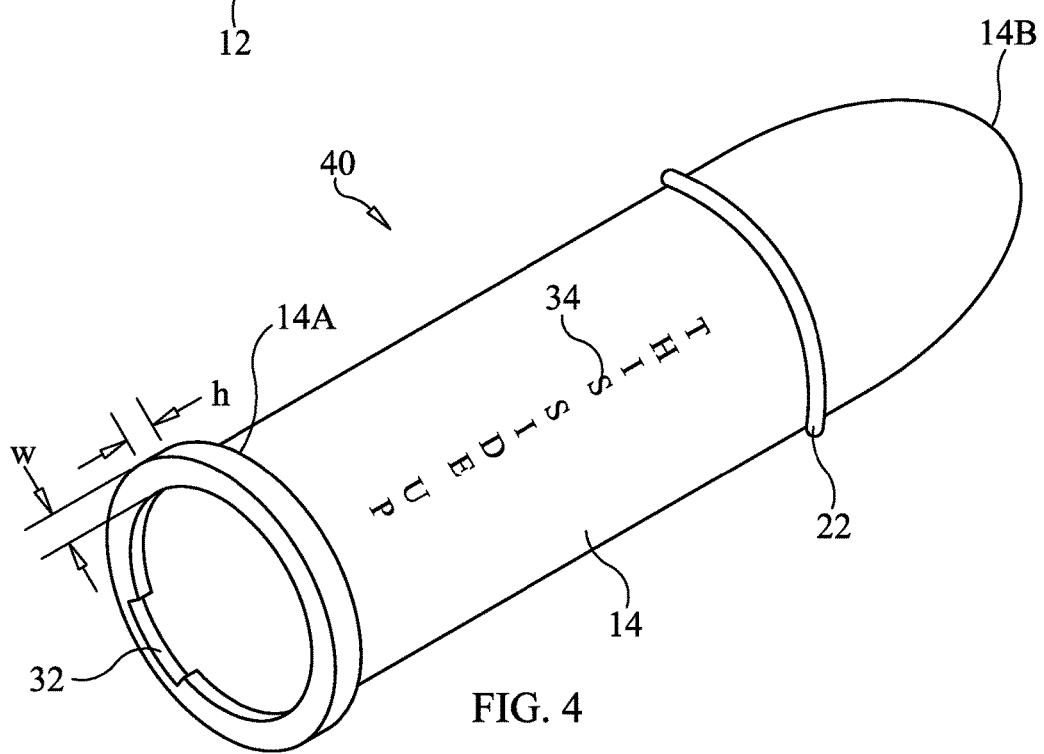
FIG. 4 is a perspective view of a condom with a notched enhanced base ring and a retention ring in accordance with another embodiment of the present invention.

Yet another embodiment of the present invention is illustrated in FIG. 4 where a condom 40 includes the elements and features of the above-described condom 30 and further includes at least one additional ring 22. The one or more additional ring(s) 22 are identical in structure and function to the previously-described ring 22 included in condom 20.

In each of the above-described embodiments of the present invention, ring 12 (with or without notch 32) is a monolithic element. However, the present invention is not limited to monolithic constructions. For example and as illustrated in FIG. 5, a condom 50 of the present invention can have its base ring constructed from a split ring 52 that defines a gap 54. Material 56 (e.g., the same or similar material used to make the rest of condom 50 or other types of condoms, similar type of condom material, etc.) can be coupled to split ring 52 and span gap 54. In this way, the assembled combination of split ring 52 and material 56 (to thereby define gap 54) replicates the structure and function of the above-described notch 32. It is to be understood that material 56 can be affixed to the outermost periphery of split ring 52 (as shown), to the inside periphery of split ring 52, both the outermost periphery and inside periphery of split ring 52, and/or one or more sides of split ring 52, without departing from the scope of the present invention.

The advantages provided by the above-described notch 32 or gap 54 can be extended to the condom's sleeve. For example, referring now to FIGS. 6-7, a condom 60 includes the features of the above-described condom 30 and further includes features to define a urethral tube void region along sleeve 14. More specifically, interior surface 14C of sleeve 14 has two axially-extending and spaced-apart ridges 62 coupled thereto or integrated therewith such that ridges 62 protrude radially into sleeve 14. Ridges 62 are spaced apart by a distance $W_v$ to thereby define a void region 64 there between that is essentially a continuation of the void defined by notch 32. That is, each of ridges 62 is aligned with an edge of notch 32. Ridges 62 can be fabricated such that their radial height "$H_r$" makes void region 64 match the radial dimension of notch 32. Ridges 62 extend axially along sleeve 14 to a point that will approximately align with the corona of a penis when condom 60 is worn. Similar to the urethral tube void provided by notch 32, $W_v$ can range from approximately 0.125 inches to approximately 0.75 inches. Indicia 66 can be provided on sleeve 14 in diametric opposition to void region 64 thereby allowing a user to readily position condom 60 on a penis such that notch 32 and void region 64 will be aligned with the penis' urethral tube. That is, when condom 60 is worn with indicia 66 facing up as described earlier herein, ridges 62 can rest against the wearer's penis on both sides of the penis' urethral tube such that the portion of sleeve 14 spanning between ridges 62 (i.e., defined by the distance $W_v$) is offset from the penis and does not apply radial inward pressure on the penis in the area of the urethral tube. A condom having the above-described urethral tube void region 64 could also be fabricated using the enhanced base ring 12 without any notch formed therein as shown in FIGS. 1A-1C. In addition, a condom having the above-described urethral tube void region 64 can have one or more additional rings (e.g., ring 12 and/or ring 22 as described above) at axial location(s) along sleeve 14.

The radial pressure provided by the enhanced base ring of the present invention as well as that provided by any additional ring(s) can contribute to and/or enhance a wearer's sexual experience. The present invention non-invasively aids the natural penis firming and erection process by impeding blood flow from the penis. The present invention non-invasively assists the holding of blood in a penis to thereby help cause and maintain an erection. Such impediment of blood flow is assisted by the above-described base ring and, when present, any additional ring(s). Thus, in general, the condom's various rings described herein apply pressure to the outside of various parts of the penis with the pressure transferring inward to provide a firmer penis and/or erection assistance. The inclusion of a urethral tube void in the enhanced base ring having a notch and/or the condom's sleeve will improve the flow of seminal or other body fluids.

The advantages of the present invention are numerous. The single-use condoms are simple and inexpensive devices that can be used when needed or desired to provide contraception, a firmer penis, and/or erection assistance. Use of each condom requires no surgery or surgical implantation, and has no medical side effects or adverse effects. The present invention can provide a better, more satisfying sexual experience than is possible with a conventional condom, as well as provide aid to those with some degree of ED caused by health issues such as heart diseases, vascular problems, prostate and other cancers, diabetes, as well as health issues caused by medications such as blood thinners and hundreds of other medications including those used for treatment of psychologically-induced sexual problems.

Although the invention has been described relative to specific embodiments thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. A condom, comprising:
    an elastic ring adapted to fit over a male penis, said elastic ring having a radial width and an axial length, said radial width defined by a first portion having a dimension in a range of approximately 0.1875 inches to approximately 0.5 inches and a second portion having a dimension less than said dimension of said first portion, said second portion spanning an arc in a range of approximately 0.125 inches to approximately 0.75 inches, said axial length being in a range of approximately 0.1875 inches to approximately 5 inches; and
    a sleeve of flaccid and elastic material having an annular open end and a closed end, said sleeve being coupled to said elastic ring.

2. A condom as in claim 1, wherein said second portion faces radially inward of said elastic ring and extends along said axial length.

3. A condom as in claim 2, further comprising indicia on said sleeve and in diametric opposition to said second portion.

4. A condom as in claim 2, further comprising at least one elastic retention ring coupled to said sleeve.

5. A condom as in claim 1, further comprising indicia on said sleeve and in diametric opposition to said second portion.

6. A condom as in claim 5, further comprising at least one elastic retention ring coupled to said sleeve.

7. A condom as in claim 1, further comprising at least one elastic retention ring coupled to said sleeve.

8. A condom as in claim 1, wherein said elastic ring is monolithic.

9. A condom as in claim 1, wherein said elastic ring is assembled.

10. A condom as in claim 1, wherein said sleeve has an interior surface, and further comprising a pair of spaced-apart ridges coupled to and extending axially along said interior surface, each of said ridges aligned with an edge of said second portion.

* * * * *